United States Patent [19]

Tseng

[11] Patent Number: 5,679,633
[45] Date of Patent: Oct. 21, 1997

[54] LOW FOAM BRANCHED ALKYLDIMETHYLAMINE OXIDES

[75] Inventor: Chuen-Ing Jeannie Tseng, Lawrenceville, N.J.

[73] Assignee: Lonza Inc., Fair Lawn, N.J.

[21] Appl. No.: 544,277

[22] Filed: Oct. 17, 1995

Related U.S. Application Data

[62] Division of Ser. No. 246,688, May 20, 1994, Pat. No. 5,486,315.

[51] Int. Cl.$^6$ .................. C11D 1/75; C11D 1/88
[52] U.S. Cl. ............ 510/499; 510/503; 510/237; 510/218; 510/490; 510/500; 510/504; 510/535; 510/480
[58] Field of Search .................. 564/297; 252/547, 252/106, 546, DIG. 7; 134/22.1, 40; 510/503, 237, 218, 490, 500, 504, 535, 480

[56] References Cited

U.S. PATENT DOCUMENTS

| | | | |
|---|---|---|---|
| 3,093,591 | 6/1963 | Freese | 252/106 |
| 3,336,387 | 8/1967 | Finch | 260/583 |
| 3,387,178 | 6/1968 | Fields | 260/583 |
| 3,484,523 | 12/1969 | Findlan | 424/248 |
| 3,496,110 | 2/1970 | Shumway | 252/142 |
| 3,754,033 | 8/1973 | Shay | 260/567.6 M |
| 4,113,631 | 9/1978 | Thompson | 252/8.55 C |
| 4,203,872 | 5/1980 | Flanagan | 252/542 |
| 4,229,313 | 10/1980 | Joy | 252/98 |
| 4,264,479 | 4/1981 | Flanagan | 252/524 |
| 4,287,080 | 9/1981 | Siklosi | 252/104 |
| 4,287,102 | 9/1981 | Miyajima | 252/547 |
| 4,425,243 | 1/1984 | Green | 252/8.5 C |
| 4,450,174 | 5/1984 | Green | 424/329 |
| 4,576,728 | 3/1986 | Stoddart | 252/102 |
| 4,650,904 | 3/1987 | Fujita | 564/298 |
| 4,659,565 | 4/1987 | Smith | 424/70 |
| 4,783,283 | 11/1988 | Stoddart | 252/547 |
| 4,921,627 | 5/1990 | Copeland | 252/99 |
| 4,938,893 | 7/1990 | Copeland | 252/527 |
| 5,164,120 | 11/1992 | Borland et al. | 252/546 |
| 5,252,245 | 10/1993 | Garabedian, Jr. et al. | 252/153 |
| 5,389,282 | 2/1995 | Saijo et al. | 252/174.17 |

FOREIGN PATENT DOCUMENTS

| | | |
|---|---|---|
| 747963 | 12/1966 | Canada. |
| 0 267 662 | 5/1988 | European Pat. Off.. |
| 1567214 | 4/1969 | France. |
| WO 92/13934 | 8/1992 | WIPO. |

OTHER PUBLICATIONS

Ralston, A. W. et al., "The Solubilities of Long-chain Dialkyldimethylammonium Chlorides in Organic Solvents," *J. Org. Cham.*, 13 (Mar. 1948), 186–190.

Primary Examiner—Paul Lieberman
Assistant Examiner—Charles I. Boyer
Attorney, Agent, or Firm—Darby & Darby

[57] ABSTRACT

An amine oxide having the formula:

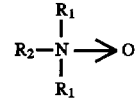

wherein the $R_1$ groups are independently selected from $C_1$–$C_4$ alkyl or alkoxy groups and $R_2$ is a branched chain $C_{11}$–$C_{16}$ alkyl group; a detersive composition containing such amine oxide with amphoteric surfactants and/or alkalizing agent; and the use of said composition for cleaning hard surfaces.

16 Claims, No Drawings

LOW FOAM BRANCHED ALKYLDIMETHYLAMINE OXIDES

This is a division, of application Ser. No. 08/246,688, filed May 20, 1994 now U.S. Pat. No. 5,486,315.

BACKGROUND OF THE INVENTION

Trialkylamine oxides are well known as surfactants and foaming agents that are used in a variety of applications, including sanitizers, cleaners, emulsifiers, fabric softeners, oil drilling lubricants, and the like. The particular application for which a given amine oxide will be preferred depends upon its functional characteristics, which in turn depend upon the nature of the alkyl substituents. The functional properties include surface tension reduction, wetting ability, and the amount and quality of the foam produced. Structural parameters include the number of long-chain alkyl groups, their length, and their degree of branching.

For example, U.S. Pat. No. 4,425,243 discloses n-octyl dimethylamine oxide, n-decyl dimethylamine oxide, and branched decyl dimethylamine oxide for use in oil and gas production, based on their ability to produce copious, stable foam. U.S. Pat. No. 4,113,631 discloses his (2-hydroxyethyl) cocoamine oxide; dimethyl-hydrogenated tallowamine oxide, and dimethylhexadecylamine oxide, all of which contain unbranched alkyl chains, for use in combination with quaternary ammonium compounds as foaming and silt suspending agents. European Patent Application WO 92/13934 teaches the use of N-alkyl-N,N,-dimethylamine oxides (preferably containing a $C_{12-18}$ straight chain alkyl group), in combination with N,N-dehydrogenated tallow N,N,-dimethylammonium chloride, in laundry rinses and dryer sheets; no evaluation of the foaming properties of these formulations is disclosed. U.S. Pat. No. 4,921,627 discloses a relatively low-foaming amine oxide containing two $C_6$–$C_{20}$ straight-chain or branched-chain alkyl groups.

Unfortunately, none of these products has little or no foam, while at the same time exhibiting superior surface tension reduction and wetting characteristics. The need for such compounds in sanitizing and cleaning applications, where high foam production is detrimental, is apparent for clean-in-place and machine cleaning applications.

BRIEF DESCRIPTION OF THE INVENTION

It has now been found that selected amine oxides provide superior surface tension reduction and wetting characteristics while producing little or no stable foam. These compounds can be synthesized from relatively inexpensive components and are stable in formulations appropriate for use in commercial applications.

The compounds of this invention are unique amine oxides, particularly isododecyldimethylamine oxide and isotridecyldimethylamine oxide, for use as low-foaming surfactants.

The invention further provides unique amine oxides that are stable in bleach and in other formulations useful for clean-in-place and machine-cleaning applications.

These and other objects of the invention will be apparent to those of ordinary skill in the art in light of the detailed description below.

DETAILED DESCRIPTION OF THE INVENTION

The branched trialkylamine oxides of the present invention have the following structure

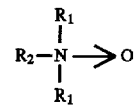

wherein the R1 groups are independently selected from $C_1$–$C_4$ alkyl or alkoxy groups and $R_2$ is a branched chain $C_{11}$–$C_{16}$ alkyl group. For $R_1$, methyl, ethyl, and hydroxyethyl are preferred and methyl is most preferred. For $R_2$, branched $C_{12}$ and $C_{13}$ (idododecyl and isotridecyl) groups are preferred.

Typically, alkyldimethylamine oxides are synthesized from alcohols, which are halogenated and reacted with dimethylamine to form alkyldimethylamine. This compound is then converted to the corresponding amine oxide by reaction with hydrogen peroxide.

The starting alcohols are available from Exxon Chemical Company under the trade name EXXAL. The EXXAL products are mixtures of branched primary alcohols which are produced by catalytic hydroformylation or carbonylation of higher olefin feedstocks. As an example, EXXAL 12 is a mixture of $C_{10}$–$C_{14}$ primary alcohols having the following carbon distribution (weight %): $C_{10}$, 6%, $C_{11}$; 18%, $C_{12}$, 55%; $C_{13}$, 20%; $C_{14}$, 1%. The major isomers are trimethyl-1-nonanols and tetramethyl-1-nonanols. Since the reaction conditions that convert the branched alcohols to alkyl dimethyl amine oxides are relatively mild and preclude substantial rearrangements, the $R_2$ branched alkyl substituent of the amine oxide reflects the same isomer distribution and branching structures as that found in the starting alcohol preparation.

The alcohols are halogenated by reaction with phosphorus tribalides having the formula $PX_3$, wherein X is chloride, bromide, or iodide. In a preferred embodiment, $PCl_3$ is used, and the chlorination reaction is carried out as described in Example 1 below.

The alkyl halides that result from the above reaction are then reacted with dimethylamine in the presence of sodium hydroxide to produce alkyldimethylamines. Preferably, the molar ratio of dimethylamine to alkyl halide in the reaction is around 3:1.

Finally, the alkyldimethylamines are treated with hydrogen peroxide to form alkyldimethylamine oxides.

Table 1 shows the useful and preferred reaction conditions for the above synthetic steps.

TABLE 1

| Synthesis of | Temperature (°C.) | | Molar Ratio | | |
|---|---|---|---|---|---|
| | Useful | Preferred | Ratios | Useful | Preferred |
| Alkyl Halides | 100–180 | 120–160 | ROH/PCl$_3$ | 1–1.2 | 1–1.05 |
| Trialkylamine | 140–220 | 150–190 | RX/DMA | 1–5 | 2–4 |
| Triakylaniine Oxides | 50–110 | 70–90 | H$_2$O$_2$/Trialkylamine | 1–1.2 | 1.03–1.1 |

The amine oxides of the present invention were evaluated using the following Standard Applications Methods (SAPM), which are described below:

Dynamic Surface Tension Measurements

These measurements were conducted with the SensaDyne Surface Tensiometer model 6000, which utilized the maximum bubble pressure method of surface tension analysis. Surface tension profiles of the amine oxides at the desired concentrations were measured in deionized water at 25° C.

Ross-Miles Foam Height Test (ASTMD1173-53)

Ross-Miles foam height measurements were taken at 25° C. Two hundred ml of a test solution at the desired concentration were dropped through a cylinder impacted with 50 ml of the same solution. Due to the impacting force, foam was generated and its height measured initially and at 5 minutes.

The Dynamic Foam Test

This method monitors foam generation at room temperature over time. A surfactant solution is pumped through an aspirator straight down into a clear glass cylinder (9.5"× 24"). To compare isododecyl dimethylamine oxide with other surfactants, solutions with a total surfactant concentration of 1000 ppm are used. The diluted solution is pumped through 1 inch tubing at a flow rate of 5 ft/sec. The foam height is measured at 1 and 5 minutes after the pump is started.

Drayes Wetting Time

This method was used to determine the efficiency as wetting agents at 25° C. A Weighted cotton skein was dropped into a 500 ml solution. The time required for the skein to relax was recorded as the Drayes wetting time. At least three determinations were averaged for each sample.

The amine oxides of the present invention can be blended with other compounds to provide formulations useful in a variety of industrial and other applications in which low foam, high surface tension reduction, and fast wetting times are desired. Non-limiting examples of such compounds include alkalizing agents, amphoteric surfactants, quaternary ammonium compounds, sequestering agents, dyes, and fragrances. In general, these agents should not contribute significant amounts of foam to the formulation. In the case of the amine oxide/amphoteric surfactant blends, the weight ratio is generally between 5/1 and about 1/5.

Examples of alkalizing agents that can be used with the amine oxides include sodium hydroxide, sodium carbonate, and sodium metasilicate.

Amphoteric surfactants include disodium cocoamphodiacetate (Amphoterge W-2), sodium cocoamphoacetate (Amphoterge W), disodium cocoamphodipropionate (Amphoterge K-2), disodium capryloamphodipropionate (Amphoterge KJ-2, all trade mark of Lonza). In Amphoterge KH-2 the alkyl group is $C_6$–$C_8$.

The amine oxides of the present invention with quaternary ammonium compounds in sanitizer applications are described in a co-pending U.S. Patent application by L. K. Hall and M. Y. Chiang entitled "Low Foam Sanitizers", filed on even date herewith, which disclosure is hereby incorporated by reference herein.

The detersive compositions of the invention are conventionally sold in the form of concentrates of the active ingredients. The following table shows the percent active in the formulations:

TABLE 2

| Compound (% solids) | Broad Range wt. % | Preferred Range wt. % |
|---|---|---|
| Amine Oxide | 0.5–20 | 1–15 |
| Amphoteric Compounds | 0.5–20 | 1–5 |
| Alkalizing Agents | 1–10 | 1–5 |

When applied to hard surfaces, the aforesaid concentrates are diluted with water to form use dilutions which contain from 100 to 1000 ppm, preferably from 200 to 800 ppm of the amine oxide.

The final formulations may also include from 1 to 5% of a sequestering agent such as ethylenediaminetetraacetic acid (EDTA), from 1 to 15% of a pH regulator such as sodium hydroxide, and from 0.01 to 1% of dyes and fragrances such as those commonly used in the art in cleaning and disinfecting solutions.

Non-limiting examples of the applications in which the amine oxides can be used include clean-in-place and machine cleaning applications, such as are required in dairy plants and meat packaging plants.

The following Examples describe the synthesis and evaluation and application of the trialkyl amine oxides of the present invention. These Examples are intended to illustrate the invention without limiting its scope.

Example 1—Synthesis of Isododecyl Dimethylamine Oxide

A. Synthesis of Isododecyl Chloride

To a 1-gallon glass-line pressure reactor was charged 715 grams of phosphorus trichloride ($PCl_3$, 5.2 moles). To the reactor was charged 2790 grams of isododecyl alcohol (Exxal 12, 15.0 moles) via an addition pump over a period of one hour while maintaining the reaction temperature below 100° C. After addition, the mixture was stirred at 130°–135° C. for 3 hours and cooled. The top organic layer was collected, yielding 2733 grams (94.5%) of isododecyl chloride.

B. Preparation of Isododecyldimethylamine

In a 1-gallon stainless steel autoclave was charged 4.5 moles of isododecyl chloride, 13.5 moles of dimethylamine (as 40% aqueous solution), and 4.5 moles of sodium hydroxide (as 50% aqueous solution). The mixture was heated at 175°–190° C. for 6 hours. The mixture was cooled. The top organic layer was collected and the residual dimethylamine evaporated. The isododecyldimethylamine was obtained in 98.1% yield.

C. Preparation of Isododecyldimethyiamine Oxide

In a 500 ml reaction flask was charged 0.5 mole of isododecyldimethylamine. The content of the flask was heated to 70° C. A solution of 0.515 moles of hydrogen peroxide (as 30% aqueous solution) in 100 grams of de-ionized water was added while maintaining the temperature of the reaction at 75°–80° C. After addition, the reaction was stirred at 80° C for 4 hours. Analysis showed 98.4% conversion of starting amine to isododecyldimethylamine oxide.

Example 2—Evaluation of Surfactant Properties of Alkyldimethylamine Oxides

When the amine oxides are used in combination with the amphoteric surfactants, at least 10 ppm, preferably 100 to 2,000 ppm, of each compound is present. The series of amine oxides were tested for their surface tension reduction properties, Drayes wetting time, and Ross-Miles foam height. In all cases, the products were tested at 1000 ppm actives in deionized water. Table 3 shows a comparison of the properties of these amine oxides.

TABLE 3

| Alkyl DMAO | Alcohol Source | Surface Tension (dynes/cm) | Draves Wetting (min:sec) | Ross-Miles Foam (mm) Initial | 5 min |
|---|---|---|---|---|---|
| Isododecyl | Exxal 12 (Exxon) | 33 | 0:15 | 90 | 0 |
| Isotridecyl | Exxal 13 (Exxon) | 30.5 | 0:06 | 115 | 8 |
| Isooctyl | Exxal 8 (Exxon) | 62.9 | >4:00 | 0 | 0 |
| 2-Ethylhexyl | 2-Ethylhexyl alcohol (Aldrich) | 64.1 | >4:00 | 0 | 0 |
| Isononyl | Exxal 9 (Exxon) | 56.2 | >4:00 | 0 | 0 |
| Isodecyl | Exxal 10 (Exxon) | 51 | >4:00 | 8 | 0 |
| Isostearyl | Exxal 18 (Exxon) | 35.8 | 0:12 | 64 | 64 |
| Decyl | Decyl alcohol (Vista) | 48 | >3:00 | 20 | 0 |
| Dodecyl | Dodecyl alcohol (Vista) | 36 | 0:18 | 140 | 130 |

The influence of the structure of the long-chain alkyl group on surfactant properties is evident. Isododecyl dimethylamine oxide and isotridecyldimethylamine oxide (containing branched $C_{12}$ and $C_{13}$ groups respectively) both produce little or no stable foam and, at the same time, exhibit the most pronounced surface tension reduction capabilities and shortest Draves wetting times of all the tested compounds. By contrast, dimethylamine oxide containing a non-branched $C_{12}$ group (dodecyl), and that containing a branched $C_{18}$ group (isostearyl), both produce significant amounts of stable foam, while exhibiting adequate surface tension reduction and short Draves wetting times. Conversely, compounds that incorporate an unbranched $C_{10}$ group (decyl) or branched chains of $C_8$–$C_{10}$ (isooctyl, 2-ethylhexyl, isononyl, and isodecyl) exhibit inadequate surface tension reduction and long wetting times, even though they produce little or no foam. Thus, the preferred embodiments of the present invention, isododecyl dimethylamine oxide and isotridecyl dimethylamine oxide, are clearly superior as low-foaming surfactants according to these criteria.

Example 3—Comparison of Surfactant Properties

The surfactant properties of isododecyldimethylamine oxides are compared with non-ionic surfactants commonly used in the formulation. Examples are Pluronic L-61, nonylphenol ethoxiates and linear alcohol ethoxylates.

It is clear from these data that nonylphenolethoxylates and linear alcohol ethoxylates generate much higher foam and have much higher cloud points. Pluronic L-61, while produced low foam, has much longer wetting time.

The following Examples 4 through 8 are cleaning compositions that are formulated using isododecyldimethylamine oxide.

| INGREDIENTS | % WT |
|---|---|
| Example 4 - Low Foam Floor Cleaner Formulation | |
| Isododecyldimethylamine Oxide (30%) | 11.0 |
| Tetrapotassium Pyrophosphate | 14.0 |
| Sodium Metasilicate (anhydrous) | 5.0 |
| De-Ionized Water | 70.0 |
| Total | 100.0 |
| Example 5 - Bottle Wash Formulation | |
| Amphoterge KJ-2 | 2.0 |
| Isododecyldimethylamine Oxide | 2.0 |
| Sodium Gluconate | 5.0 |
| Potassium Hydroxide (50% Aqueous Solution) | 12.0 |
| De-Ionized water | 79.0 |
| Total | 100.0 |

TABLE 4

| Surfactants | Source | Surface tension (dynes/cm) | Draves Wetting (min:sec) | Dynamic Foam (in) | Ross-Miles Foam (mm) initial | 5 min. | Cloud Point (°C.) |
|---|---|---|---|---|---|---|---|
| isododecyl dimethylamine oxide | | 33 | 0:15 | 0.5 | 90 | 0 | none |
| Pluronic L-61 (ethylene oxide/propylene oxide blocked copolymer) | BASF | 42 | cloudy | 0.5 | 0 | 0 | 24 |
| Carsonon-9 (nonylphenol, 9 mole ethoxylates) | LONZA | 40 | 0:07 | 4.8 | 95 | 70 | 54 |
| Caronon-12 (nonylphenol, 12 mole ethoxylates) | LONZA | 41 | 0:11 | >9.0 | 115 | 90 | 81 |
| Neodol 91-6 ($C_{9-11}$ alcohol ethoxylates, 6 mole EO) | Shell Chemical | 31 | 0:05 | >9.0 | 129 | 115 | 53 |
| Neodol 91-8 ($C_{9-11}$ alcohol ethoxylates, 8 mole EO) | Shell Chemical | 34 | 0:11 | >9.0 | 135 | 122 | 80 |

| INGREDIENTS | % WT |
|---|---|
| Example 6 - Carpet Shampoo Formulation | |
| Tetrasodium EDTA | 5.0 |
| Amphoterge KJ-2 | 3.0 |
| Isododecyldimethylamine Oxide | 2.0 |
| Tripotassium Pyrophosphate | 5.0 |
| Sodium Sesquicarbonate | 5.0 |
| Color, Fragrance | qs |
| De-Ionized Water | 80.0 |
| Total | 100.0 |
| Example 7 - Hypochlorite Tub and Tile Cleaner | |
| Sodium Hypochlorite (5.7%) | 52.6 |
| Sodium Hydroxide (30%) | 1.0 |
| Isododecyldimethylamine Oxide | 1.5 |
| De-Ionized Water | 44.9 |
| Total | 100.0 |
| Example 8 - Wax Stripper (Solvent) | |
| Tetrasodium EDTA | 1.0 |
| Amphoterge KJ-2 | 2.0 |
| Propylene glycol n-Butyl Ether | 4.0 |
| Isododecyldimethylamine Oxide (30%) | 3.0 |
| De-Ionized Water | 90.0 |
| Total | 100.0 |

What is claimed is:

1. A method for cleaning hard surfaces that comprises contacting said hard surface with a detersively effective amount of a detersive composition comprising:
   a) a first component consisting essentially of at least one amine oxide of the structure:

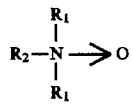

wherein the $R_1$ groups are independently selected from $C_1$–$C_4$ alkyl or alkoxy groups and $R_2$ is a branched chain $C_{11}$–$C_{15}$ alkyl group having from 3 to 4 methyl branches; and
   b) an amphoteric surfactant; wherein the weight ratio of said amine oxide and amphoteric surfactant is between about 5/1 and about 1/5.

2. The method of claim 1, wherein said amine oxide and the amphoteric surfactant are each present in at least 10 ppm.

3. The method of claim 1, wherein the concentrations of said amine oxide and the amphoteric surfactant are each between about 100 ppm and about 2000 ppm.

4. The method of claim 1, wherein $R_1$ is a methyl group.

5. The method of claim 1, wherein $R_2$ is a $C_{12}$ alkyl group.

6. The method of claim 1, wherein $R_2$ is a $C_{13}$ alkyl group.

7. The method of claim 1 wherein $R_2$ is a tri- or tetramethylnonyl group.

8. The method of claim 1, wherein said amphoteric compound is disodium capryloamphodipropionate.

9. The method of claim 1, wherein the composition is a concentrate and the concentration of said amine oxide is between about 0.5% and 20% by weight, and the concentration of the amphoteric surfactant is between about 0.5% and about 20% by weight, based on the total weight of the detersive composition.

10. The method of claim 1, wherein the composition is a concentrate and the concentration of said amine oxide is between about 1% and about 15% by weight, and the concentration of the amphoteric surfactant is between about 1% and about 5% by weight, based on the total weight of the detersive composition.

11. A method for cleaning hard surfaces that comprises contacting said hard surface with a detersively effective amount of a detersive composition comprising:
   a) a first component consisting essentially of at least one amine oxide selected from the group consisting of isododecyldimethylamine oxide and isotridecyidimethylamine oxide; and
   b) an amphoteric surfactant; wherein the weight ratio of said amine oxide and amphoteric surfactant is between about 5/1 and about 1/5.

12. The method of claim 11, wherein said amine oxide and the amphoteric surfactant are each present in at least 10 ppm.

13. The method of claim 11, wherein the concentrations of said amine oxide and the amphoteric surfactant are each between about 100 ppm and about 2000 ppm.

14. The method of claim 11, wherein said amphoteric compound is disodium capryloamphodipropionate.

15. The method of claim 11, wherein the composition is a concentrate and the concentration of said amine oxide is between about 0.5% and 20% by weight, and the concentration of the amphoteric surfactant is between about 0.5% and about 20% by weight, based on the total weight of the detersive composition.

16. The method of claim 11, wherein the composition is a concentrate and the concentration of said amine oxide is between about 1% and about 15% by weight, and the concentration of the amphoteric surfactant is between about 1% and about 5% by weight, based on the total weight of the detersive composition.

* * * * *